United States Patent
Sun et al.

(10) Patent No.: US 8,198,485 B2
(45) Date of Patent: Jun. 12, 2012

(54) RESOLUTION OF 4,5-DIMETHOXY-1-(METHYLAMINO-MENTHYL)-BENZOCYCLOBUTANE

(75) Inventors: Piaoyang Sun, Jiangsu (CN); Yongjiang Chen, Jiangsu (CN); Guangliang Yu, Jiangsu (CN)

(73) Assignee: Jiangsu Hengrui Medicine Co., Ltd., Jiangsu (CN)

( * ) Notice: Subject to any disclaimer, the term of this patent is extended or adjusted under 35 U.S.C. 154(b) by 275 days.

(21) Appl. No.: 12/742,632

(22) PCT Filed: Oct. 10, 2008

(86) PCT No.: PCT/CN2008/001711
§ 371 (c)(1),
(2), (4) Date: May 12, 2010

(87) PCT Pub. No.: WO2009/062377
PCT Pub. Date: May 22, 2009

(65) Prior Publication Data
US 2012/0004463 A1   Jan. 5, 2012

(30) Foreign Application Priority Data

Nov. 16, 2007  (CN) .......................... 2007 1 0188301
May 19, 2008  (CN) .......................... 2008 1 0093266

(51) Int. Cl.
*C07B 57/00*   (2006.01)
(52) U.S. Cl. ........................................................ 564/304
(58) Field of Classification Search .................. 564/304
See application file for complete search history.

(56) References Cited

U.S. PATENT DOCUMENTS 5,296,482 A    3/1994  Peglion et al.
6,982,350 B2 *  1/2006  Lerestif et al. ................ 564/304

FOREIGN PATENT DOCUMENTS

CN          1699331 A    2/2005

* cited by examiner

*Primary Examiner* — Porfirio Nazario Gonzalez
(74) *Attorney, Agent, or Firm* — Ryan L. Marshall; Brinks Hofer Gilson & Lione

(57) ABSTRACT

A method of resolving an important chemical intermediate, 4,5-dimethoxy-1-(methylaminomethyl)-benzocyclobutane, comprises the following steps: reacting its two enantiomers of 4,5-dimethoxy-1-(methylaminomethyl)-benzocyclobutane with di-p-toluoyl-L-tartaric acid (LDTTA) or di-p-toluoyl-D-tartaric acid (DDTTA) in an alcoholic solution or an alcohol in water solution to give the corresponding salts, and then resolving the salts. This method gives high enantiomer excess value, high yield which is more than 80% in total with normal resolution and reverse resolution.

25 Claims, No Drawings

RESOLUTION OF 4,5-DIMETHOXY-1-(METHYLAMINO-MENTHYL)-BENZOCYCLOBUTANE

The present application is the national phase application of PCT Application No. PCT/CN2008/001711, filed Oct. 10, 2008, which claims priority to Chinese Patent Application No. 200710188301.1, filed Nov. 16, 2007, and Chinese Patent Application No. 200810093266.X, filed May 19, 2008, the entireties of all of which are hereby incorporated by references.

FIELD

The present invention provides a method of resolving 4,5-dimethoxy-1-(methylaminomethyl)-benzocyclobutane (II), an important intermediate of Ivabradine, to obtain the Ivabradine intermediate (1S)-4,5-dimethoxy-1-(methylaminomethyl)-benzocyclobutane (I).

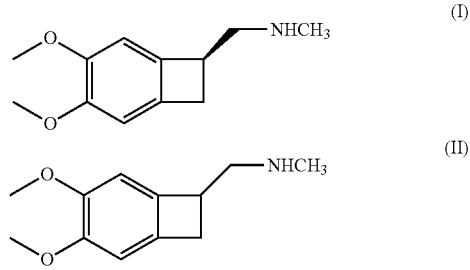

A compound of formula (I), which was prepared according to the method of the present invention, can be used for the synthesis of Ivabradine.

BACKGROUND

Ivabradine and pharmaceutically acceptable salts thereof, particularly hydrochloride thereof, have highly valuable pharmacological and therapeutic effects, especially bradycardiac effects, so that these compounds can be used not only in the treatment or prevention of various clinical symptoms of myocardial ischemia such as angina, myocardial infarction and associated rhythm disorders, but also for the treatment or prevention of various rhythm disorders, especially supraventricular rhythm disorder. Ivabradine is an effective drug of treatment of myocardial ischemia such as angina pectoris and the like.

U.S. Pat. No. 5,296,482 (the '482 patent) describes a synthetic route of Ivabradine in detail. Furthermore, the '482 patent describes a method of resolving compounds of formula (II) to obtain a compound of formula (I), using camphor sulfonic acid. However, the result of that resolving method is far from satisfactory. First, that resolving method has a very low yield. The yield of the compound of formula (I) by using camphor sulfonic acid as a resolving agent is only 4-5%, which results in the total yield of only 2-3%. Such a low yield leads to high cost and low efficiency. Second, because of the low selectivity of the resolving agent, the enantiomer excess (ee) value of the resolved product is low. Several re-crystallization steps are needed to complete the resolution of the compound. Furthermore, the process is complicated and not suitable for industrial production. The chiral purity of the final product is not satisfactory either.

In view of the medicinal value of Ivabradine and salts thereof, it is necessary to find an effective industrial method to obtain the S configuration of the intermediate compound of formula (I) with high chiral purity, in high efficiency and high yield.

DETAILED DESCRIPTION

After extensive study, the inventors have found that various commonly used acidic resolving agents are substantially ineffective for the resolution of the racemate of formula (II), except that R-Camphor sulfonic acid has certain selectivity. Some cannot react with the racemate of formula (II) to form crystalline precipitates in various solvents effectively, such as L-tartaric acid, R-mandelic acid and the like. Some can react with the racemate of formula (II) to form crystalline precipitates in solvents, but there is no selectivity and the resulting precipitates are still a racemic mixture, such as N-acetyl-L-glutamic acid, L-leucine and the like.

After extensive study, the inventors have surprisingly found that, among a large number of conventional acidic resolving agents tested, only tartaric acid diacylated by benzoyl or substituted benzoyl, such as dibenzoyl-L-tartaric acid (L-DBTA), dibenzoyl-D-tartaric acid (D-DBTA), di-p-toluoyl-L-tartaric acid (L-DTTA) or di-p-toluoyl-D-tartaric acid (D-DTTA), can resolve the (S)-amine and (R)-amine effectively.

The present invention relates to a method of resolving an important intermediate of Ivabradine i.e., 4,5-dimethoxy-1-(methyl-amino-methyl)-benzocyclobutane (II) (an amine intermediate, a racemate), comprising the step of reacting a resolving agent with said intermediate to obtain the corresponding salt in an alcoholic solvent or an alcoholic aqueous solution, and crystallizing the corresponding salt to obtain the end product (1S)-4,5-dimethyloxy-1-(methylaminomethyl)-benzocyclobutane of formula (I), wherein said resolving agent is dibenzoyl-L-tartaric acid (LDBTA), dibenzoyl-D-tartaric acid (DDBTA), di-p-toluoyl-L-tartaric acid (LDTTA) or di-p-toluoyl-D-tartaric acid (DDTTA), and preferably di-p-toluoyl-L-tartaric acid, or di-p-toluoyl-D-tartaric acid.

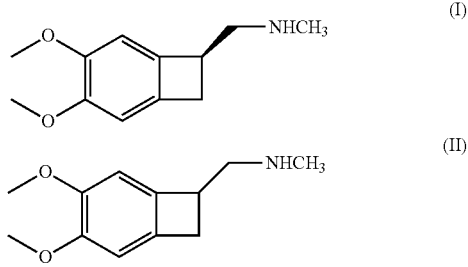

Further, the resolving method of the present invention includes a re-crystallizing step after the salt forming and crystallizing steps. The resolving agent, di-p-toluoyl-L-tartaric acid (LDTTA) and di-p-toluoyl-D-tartaric acid (DDTTA) used in the present invention, may be used alone or jointly. Specifically, the present invention relates to a method of resolving racemate of formula (II). The problem to be solved by the present invention is to obtain the above pharmaceutically acceptable optically pure compound of formula (I) of S configuration with excellent yield by using di-p-toluoyl-L-tartaric acid. The method is characterized in that the racemate of formula (II) reacts with an acidic resolving agent in a particular solvent to obtain the corresponding salt and to selectively precipitate the crystals of the salt of the desired chiral intermediate amine.

The method of resolving the compounds of formula (II) preferably includes the process of reacting the compounds of formula (II) with an acidic chiral resolving agent to obtain the corresponding salt, crystallizing the corresponding salt to form crystal precipitates, re-crystallizing the crystal precipitates to form re-crystallized precipitates, and extracting the re-crystallized precipitates to obtain the intermediate amine of formula (I). If necessary, the resolving method can further comprise the step of reacting the compound of formula (I) with an suitable acid to obtain the corresponding salt as a suitable intermediate for synthesizing Ivabradine. The compounds of formula (II) used herein are prepared according to U.S. Pat. No. 5,296,482.

With regard to the amount of the resolving agent, in theory, because an acid-base neutralization reaction needs equal numbers of moles of acid and base, the molar ratio of the intermediate amine to the resolving agent can be 2:1. If only considering forming salts with the desired configuration, the molar ratio can be 4:1. If considering forming acid addition salts with equal moles of acid and base, the molar ratio can be 1:1. However, after research, the inventors found that a higher proportion of the resolving agent gives more satisfactory yield of a resolving product with high chiral purity. Generally speaking, the suitable molar ratio of the intermediate amine to the resolving agent can be from 5:1 to 1:2, the preferable ratio is from 2:1 to 1:1. Excessive amount of the resolving agent is not more helpful for the resolution.

Said resolving process of racemate of formula (II) can be carried out in a conventional solvent, preferably in an organic solvent, more preferably in an alcoholic solvent. Moreover, the alcoholic solvent could be used alone or in combination with other organic solvents. Alcoholic solvents, as used in the present invention, include alcoholic solvents used alone as well as alcohol-based mixed solvent. Said alcoholic solvents can be lower fatty alcohol of 3 carbon atoms or less, preferably ethanol. Said alcoholic solution can be ethanol aqueous solution. Further, the resolving process of racemate of formula (II) can also be carried out in a conventional aqueous solution; preferably an alcoholic aqueous solution. The ratio of alcohol and water can vary. Preferably the proportion of the alcohol solvent is 50%~100%. Alcoholic solvents discussed herein are lower fatty alcohol of 3 carbon atoms or less, preferably ethanol.

In order to improve the chiral purity of the intermediate amine of formula (I), sometimes it is necessary for the compound of formula (I) to be re-crystallized. The resolving process can generally be carried out at room temperature; if necessary, under heating condition. Generally, the re-crystallizing step is carried out under heating condition. First, the compound of formula (I) is dissolved in a particular solvent, and then the re-crystallization is completed slowly at room temperature. In general, after re-crystallizing twice, the chiral purity is often satisfactory, and the ee value is generally above 99%.

The process to obtain the free intermediate amine from the resolved acid addition salt is conventional, wherein the base used is preferably sodium hydroxide. The extraction solvent used can be a hydrophobic organic solvent used in conventional extraction, preferably toluene, ethyl acetate, methylene chloride and chloroform, etc., more preferably ethyl acetate and chloroform. Moreover, the process of salt formation of the compound of formula (I) is also conventional. The compound of formula (I) can form a salt with a pharmaceutically acceptable acid in order to purify, or store the compound. Alternatively, the compound of formula (I) can be used directly in a further process. The acid used in the salt formation of the compound of formula (I) is preferably hydrochloric acid. The salt formation method is conventional. It can be readily performed by a person with ordinary skill in the art.

The compound of formula (I) or salts thereof according to the present invention has the cumulative resolving yield up to more than 80% and the chiral purity more than 99%, particularly suitable as a synthetic intermediate of Ivabradine and pharmaceutical acceptable salts thereof.

EXAMPLES

The present invention is illustrated by the following examples in detail which in no way should be construed as limiting the scope of the present invention.

Example 1

8.0 g (41.40 mmol) of racemate of formula (II) was dissolved in 350 mL of ethanol. To this reaction mixture, 4.0 g (10.35 mmol) of LDTTA was added. Then the reaction mixture was heated to reflux until the initially un-dissolved material thereby dissolved in the solution. After cooling, a precipitate crystallized from the reaction solution. The resulting precipitate was collected by filtration, and then was dried to obtain a crude product. It was analyzed by HPLC, showing 94.14% of S configuration.

The crude product was dissolved in 350 mL of ethanol. The reaction mixture was heated to reflux until the initially un-dissolved material thereby dissolved in the solution. After cooling, crystals precipitated from the reaction solution. The resulting precipitate was collected by filtration, and then was dried to obtain 3.47 g (5.99 mmol) of product with the resolving yield of 28.9% (the proportion of S configuration in relation to the racemate by weight). HPLC analysis showed 97.19% of S configuration.

Example 2

8.0 g (41.40 mmol) of racemate of formula (II) was dissolved in 350 mL of ethanol. To this reaction mixture, 8.0 g (20.7 mmol) of LDTTA was added. Then the reaction mixture was heated to reflux until the initially un-dissolved material thereby dissolved in the solution. After cooling, crystals precipitated from the reaction solution. The resulting precipitate was collected by filtration, and then was dried to obtain a crude product. HPLC analysis showed 96.84% of S configuration.

The crude product was dissolved in 350 ml of ethanol. The reaction mixture was heated to reflux until the initially un-dissolved material thereby went into the solution. After cooling, crystals precipitated from the reaction solution. The resulting precipitate was collected by filtration, and then was dried to obtain 4.3 g (7.42 mmol) of product with the resolving yield of 35.8%. HPLC analysis showed 99.87% of S configuration.

Example 3

8.0 g (41.40 mmol) of racemate of formula (II) was dissolved in 350 mL of ethanol. To this reaction mixture, 16.0 g (41.4 mmol) of LDTTA was added. Then the reaction mixture was heated to reflux until the initially un-dissolved material thereby dissolved in the solution. After cooling, crystals precipitated from the reaction solution. The resulting precipitate was collected by filtration, and then was dried to obtain a crude product. HPLC analysis showed 94.56% of S configuration.

The crude product was dissolved in 350 mL of ethanol. The reaction mixture was heated to reflux until the initially un-dissolved material thereby dissolved in the solution. After cooling, crystals precipitated from the reaction solution. The resulting precipitate was collected by filtration, and then was dried to obtain 7.4 g (12.77 mmol) of first resolving product with the resolving yield of 61.7%. HPLC analysis showed 99.25% of S configuration.

The resulting residual solutions during the above resolving process and re-crystallization process were combined, and then concentrated to dryness to obtain a solid. First, the solid was treated with sodium hydroxide to obtain the free amine. Second, the reaction mixture was extracted with ethyl acetate to obtain 4.7 g of racemate of formula (II) mainly with R configuration. HPLC analysis showed 73.5% of R configuration. Then the freed amine was dissolved in 350 mL of ethanol, and 14.9 g DDTTA was added for inverse resolution. The reaction mixture was heated to reflux until the initially un-dissolved material thereby dissolved in the solution. After cooling, crystals precipitated from the reaction solution. The resulting precipitate was collected by filtration, and then was dried to obtain a crude product. HPLC analysis showed 94.86% of R configuration.

The crude product of R configuration was dissolved in 350 mL of ethanol. The reaction mixture was heated to reflux until the initially un-dissolved material thereby dissolved in the solution. After cooling, crystals precipitated from the reaction solution. The resulting precipitate was collected by filtration, and then was dried to obtain 7.3 g of product of R configuration with the reverse resolving yield of 60.8%. HPLC analysis showed 99.38% of R configuration.

The residual solutions during the above reverse resolving process and re-crystallization process was combined, and then concentrated to dryness to get a solid. First, the solid was treated with sodium hydroxide to obtain the free amine. Second, the reaction mixture was extracted with ethyl acetate to obtain 2.6 g of racemate of formula (II) mainly with S configuration. HPLC analysis showed 55.5% of S configuration. Then the freed amine was dissolved in 100 mL of ethanol, and 5.0 g of LDTTA was added. The reaction mixture was heated to reflux until the initially un-dissolved material thereby dissolved in the solution. After cooling, crystals precipitated from the reaction solution. The resulting precipitate was collected by filtration, and then was dried to obtain a crude product. HPLC analysis showed 92.62% of S configuration.

The crude product was dissolved in 100 mL of ethanol. The reaction mixture was heated to reflux until the initially un-dissolved material thereby dissolved in the solution. After cooling, crystals precipitated from the reaction solution. The resulting precipitate was collected by filtration, and then was dried to obtain 2.5 g (4.31 mmol) of product. HPLC analysis showed 99.10% of S configuration.

The products obtained in the two resolutions were combined, and then treated with a sodium hydroxide aqueous solution to free the amine. The reaction mixture was extracted with ethyl acetate to obtain 3.3 g of the intermediate amine of formula (I) of S configuration with the overall resolving yield 82.5%. HPLC analysis showed 99.20% of S configuration.

Example 4

8.0 g (41.40 mmol) of racemate of formula (II) was dissolved in 350 mL of ethanol. To this reaction mixture, 7.4 g (20.7 mmol) of LDBTA was added. Then the reaction mixture was heated to reflux until the initially un-dissolved material thereby dissolved in the solution. After cooling, crystals precipitated from the reaction solution. The resulting precipitate was collected by filtration, and then was dried to obtain a crude product. HPLC analysis showed 83.37% of R configuration.

The crude product was dissolved in 350 mL of ethanol. The reaction mixture was heated to reflux until the initially un-dissolved material thereby dissolved in the solution. After cooling, crystals precipitated from the reaction solution. The resulting precipitate was collected by filtration, and then was dried to obtain 3.6 g of product. HPLC analysis showed 90.78% of R configuration.

The invention claimed is:

1. A method for resolving 4,5-dimethoxy-1-(methylaminomethyl)-benzocyclobutane, comprising:
   reacting a resolving agent with 4,5-dimethoxy-1-(methylaminomethyl)-benzocyclobutane to obtain the corresponding salt in a solvent, wherein the resolving agent is tartaric acid diacylated by benzoyl or substituted benzoyl, and
   crystallizing the corresponding salt to obtain the S-form thereof.

2. The method according to claim 1, wherein the resolving agent is selected from the group consisting of dibenzoyl-L-tartaric acid, dibenzoyl-D-tartaric acid, di-p-toluoyl-L-tartaric acid, di-p-toluoyl-D-tartaric acid, and combinations thereof.

3. The method according to claim 2, wherein the resolving agent is di-p-toluoyl-L-tartaric acid.

4. The method according to claim 2, wherein the resolving agent is di-p-toluoyl-D-tartaric acid.

5. The method according to claim 2, wherein the resolving agent is di-p-toluoyl-L-tartaric acid combined with di-p-toluoyl-D-tartaric acid.

6. The method according to claim 1, wherein the yield of the S-form is more than about 28%.

7. The method according to claim 6, wherein the yield is more than about 35%.

8. The method according to claim 7, wherein the yield is more than about 61%.

9. The method according to claim 8, wherein the yield is more than about 80%.

10. The method according to claim 1, wherein the S-form of the corresponding salt has an enantiomer excess of more than about 89%.

11. The method according to claim 10, wherein the S-form of the corresponding salt has an enantiomer excess of more than about 99%.

12. The method according to claim 1, wherein the ratio of 4,5-dimethoxy-1-(methylaminomethyl)-benzocyclobutane to the resolving agent is from about 5:1 to about 2:1.

13. The method according to claim 12, wherein the ratio of 4,5-dimethoxy-1-(methylaminomethyl)-benzocyclobutane to the resolving agent is from about 2:1 to about 1:1.

14. The method according to claim 1, wherein the solvent is an alcoholic solvent.

15. The method according to claim 14, wherein the alcoholic solvent is ethanol.

16. The method according to claim 1, wherein the solvent is an alcoholic aqueous mixed solvent.

17. The method according to claim 16, wherein the alcoholic aqueous mixed solvent has about 50%-100% alcohol.

18. The method according to claim 16, wherein the alcohol in the alcoholic aqueous mixed solvent is ethanol.

19. The method according to claim 1, further comprising:
   re-crystallizing the S-form of the corresponding salt.

20. The method according to claim 1, further comprising:
reacting the S-form of the corresponding salt with a base to obtain (1S)-4,5-dimethyl-oxy-1-(methyl-amino-methyl)-benzocyclobutane.

21. The method according to claim 20, wherein the base is sodium hydroxide.

22. A method for resolving 4,5-dimethoxy-1-(methylaminomethyl)-benzocyclobutane, comprising:
a. reacting di-p-toluoyl-L-tartaric acid with 4,5-dimethoxy-1-(methylaminomethyl)-benzocyclobutane to obtain the corresponding salt,
b. crystallizing the corresponding salt to obtain the S-form thereof, and a first residual solution with R-form and S-form thereof,
c. reacting the first residual solution with a first base to obtain a first freed 4,5-dimethyl-oxy-1-(methyl-amino-methyl)-benzocyclobutane with more R-form than S-form thereof,
d. reacting di-p-toluoyl-D-tartaric acid with the first freed 4,5-dimethoxy-1-(methylaminomethyl)-benzocyclobutane to obtain a second corresponding salt,
e. crystallizing the second corresponding salt to obtain the R-form thereof, and a second residual solution with R-form and S-form thereof,
f. reacting the second residual solution with a second base to obtain a second freed 4,5-dimethyl-oxy-1-(methyl-amino-methyl)-benzocyclobutane with more S-form than R-form thereof,
g. reacting di-p-toluoyl-L-tartaric acid with the second freed 4,5-dimethoxy-1-(methylaminomethyl)-benzocyclobutane to obtain a third corresponding salt, and
h. crystallizing the third corresponding salt to obtain the S-form thereof.

23. The method of claim 22, wherein the combined yield of the S-form is more than about 82%.

24. The method of claim 22, wherein the steps c-h are repeated to increase the yield of the S-form.

25. A method for resolving 4,5-dimethoxy-1-(methylaminomethyl)-benzocyclobutane, comprising:
reacting a resolving agent with 4,5-dimethoxy-1-(methylaminomethyl)-benzocyclobutane to obtain the corresponding salt, wherein the resolving agent is tartaric acid diacylated by benzoyl or substituted benzoyl, and
crystallizing the corresponding salt to obtain the L-form thereof.

* * * * *